United States Patent
Schirra et al.

(10) Patent No.: US 6,815,561 B2
(45) Date of Patent: Nov. 9, 2004

(54) METHOD FOR PRODUCING DNDA

(75) Inventors: Rainer Schirra, Lohmar (DE); Heinz-Gerd Emans, Niederkassel (DE); Leonard Lichtblau, Cologne (DE)

(73) Assignee: DynITEC GmbH, Troisdorf (DE)

( * ) Notice: Subject to any disclaimer, the term of this patent is extended or adjusted under 35 U.S.C. 154(b) by 0 days.

(21) Appl. No.: 10/362,297

(22) PCT Filed: Aug. 30, 2001

(86) PCT No.: PCT/EP01/10023

§ 371 (c)(1),
(2), (4) Date: Jun. 2, 2003

(87) PCT Pub. No.: WO02/26692

PCT Pub. Date: Apr. 4, 2002

(65) Prior Publication Data

US 2003/0191346 A1 Oct. 9, 2003

(30) Foreign Application Priority Data

Aug. 30, 2000 (DE) ......................................... 100 42 862

(51) Int. Cl.$^7$ ..................... C07C 241/00; C07C 243/02
(52) U.S. Cl. ..................................................... 564/109
(58) Field of Search ......................................... 564/109

(56) References Cited

U.S. PATENT DOCUMENTS 2,856,429 A * 10/1958 Sauer .......................... 564/109
4,476,322 A * 10/1984 Chang et al. ............... 564/109

* cited by examiner

*Primary Examiner*—Brian Davis
(74) *Attorney, Agent, or Firm*—Fulbright & Jaworski L.L.P.

(57) ABSTRACT

The invention relates to a method for producing DNDA that is advantageous in economical, chemical and process engineering terms.

34 Claims, No Drawings

METHOD FOR PRODUCING DNDA

This application is a 371 of PCT/EP01/10023 filed Aug. 30, 2001.

Heretofore the energetic plasticizer DNDA-6-7, a ternary mixture of N,N'-dimethylbis-nitramine (DNDA-5; approx. 43%), N-methyl-N'-ethyl-bisnitramine (DNDA-6; approx. 45%) and N,N'-diethylbisnitramine (DNDA-7; approx. 12%), has been made in the following manner:

1. Nitration of N,N'-dimethylurea
   1.1. Batch reaction with an acid mixture (mixture of nitric acid and sulfuric acid) with the addition of urea dissolved in dichloromethane at about −10° C.
   1.2. Stopping the reaction by pouring it onto ice water.
   1.3. Collecting the reaction mixture (main product: dinitridimethylurea) in dichloromethane by shaking it out.
   1.4. Neutralizing the dichloromethane with sodium hydrogen carbonate.
2. Hydrolysis of the dinitrodimethylurea.
   2.1. Mixing the dichloromethane phase with water, evaporating the dichloromethane, followed by hydrolysis at about 100° C.
   2.2. Collecting the methylnitramine in dichloromethane
3. Nitration of N,N'-diethylurea.
   3.1. Batch reaction with a mixture of acids (mixture of nitric acid and sulfuric acid) with the addition of the urea dissolved in dichloromethane at about −15° C.
   3.2. Stopping the reaction by pouring it onto ice water.
   3.3. Collecting the reaction mixture (main product dinitrodiethylurea) in dichlormethane by shaking.
   3.4. Neutralizing the dichloromethane phase with sodium hydrogen carbonate.
4. Hydrolysis of the dinitrodiethylurea.
   4.1. Mixing the dichloromethane phase with water, evaporating the dichloromethane, followed by hydrolysis at about 100° C.
   4.2. Collecting the ethylnitramine in dichloromethane.
5. Condensation
   5.1. Condensing the methyl and ethyl nitramine in common in a fixed ratio of about 2:1 at max. 0° C. with 70% sulfuric acid and p-formaldehyde in dichloromethane.
   5.2. Stopping the reaction by pouring onto ice water.
   5.3. Collecting the reaction mixture (ternary mixture of the nitramines) in dichloromethane by shaking.
   5.4. Neutralizing the dichoromethane phase with sodium hydrogen carbonate.

The method outlined above is not capable of producing large amounts of the plasticizer in an economically practical manner.

It was therefore the problem of the invention to provide a method for producing a DNDA type plasticizer, especially a method for the production of DNDA-6-7.

This problem was solved by a method in which the following changes were made in the method known in the state of the art:

Instead of the acid mixture, highly concentrated nitric acid is used in a definite excess, preferably about an 11-fold molar excess. This change makes it possible to recycle the nitric acid; also, surprisingly few byproducts are formed.

The ureas are not dissolved in dichloromethane, but are used in solid form. The advantages of this variant: less volume of liquid, no dilution effect.

N,N' dimethylurea and N,N'-diethylurea are not nitrated separately but together at max. 5° C. in the desired molar ratio, preferably a molar ratio of about 2:1 (DNDA-5-7). The advantage is that process steps can be eliminated.

The reaction mixture (main products: dinitrodimethylurea and dinitrodiethylurea) is collected in dichloromethane by counter-current extraction. This saves process steps and the separation efficiency is optimized.

Combined hydrolyzation of the mixture thus obtained, at about 100° C., in the given molar ratio. Advantage: saving of process steps.

The entire reaction is performed continuously. Thus it is possible to remove the reaction heat more easily, the reaction volumes are reduced, thereby reducing potential dangers.

With the changes according to the invention, of the method known in the state of the art, it is possible to produce DNDA directly in a high yield, with a high purity, and in the desired composition.

By means of an HPLC study it was surprisingly found that both the desired products and the desired compositions are produced and that additional byproducts are not formed by this kind of conduct of the process of the invention.

It is expressly pointed out that it is not necessary to perform all of the steps of the process in the manner according to the invention. An improvement of the method described in the state of the art is achieved when at least one of them is performed. An especially preferred practice of the method, however, is the combining of all of the variants of the invention.

The following examples are intended to further explain the invention without limiting it.

Common Nitration of the Ureas:

355 ml of $HNO_3$ (100%) is chilled to −15° C. A mixture of 25 g of diethylurea and 50 g of dimethylurea was added in portions with vigorous stirring. In the meantime the temperature is not to exceed −10° C. The stirring time after the addition is completed was another 30 min. The reaction solution was then fed onto ice water and collected by repeatedly, preferably four times, shaking it out in 250 ml of methylene chloride each time. Neutralization was performed with an aqueous bicarbonate solution.

Combined Hydrolysis of the Dinitrodimethyl and Dinitrodiethyl Ureas:

A mixture of 1000 ml of the above solution and 540 ml of water was heated in the oil bath. At first an evaporation of the methylene chloride phase took place at bottom temperatures of about 50° C. After changing over to reflux cooling the mixture was hydrolyzed over a period of several hours, preferably over a period of about 3 h, at a bottom temperature of about 96° C. The separation of the nitramine mixture was performed by repeated shaking, preferably three times, with about 500 ml of dichloromethane each time. By evaporation in the rotary evaporator the nitramine solution was concentrated to about 95 ml.

Condensation:

At 0° C., 5 g of paraformaldehyde dissolved in 40 ml of methylene chloride was added to 120 ml of sulfuric acid (75%) in a receiver. The 95 ml of nitramine solution from the previous step was slowly added from a dropping funnel over a period of 30 minutes, with stirring. To keep the concentration of the sulfuric acid approximately constant, and to optimize the yield, 96% sulfuric acid was additionally added. The temperature in this case should preferably not rise above 0° C. The condensation was stopped after about 3 h of stirring by pouring out onto ice water, and the product was again collected in methylene chloride, neutralized, washed, and concentrated by evaporation. Yield: 35 g of DNDA-5-7.

By the method of the invention it is thus possible for the first time to produce DNDA economically, chemically and by a practical technical process, in a high yield, high purity and in the desired composition.

What is claimed is:

1. A method comprising
    nitrating both N,N'-dimethylurea and N,N'diethylurea with highly concentrated nitric acid to produce dinitrodimethylurea and dinitrodiethylurea,
    hydrolyzing the dinitrodimethylurea and dinitrodiethylurea to produce methylnitramine and ethylnitramine and other reaction products; and
    condensing the methylnitramine and ethylnitramine to form DNDA.

2. The method according to claim 1, wherein said N,N'-dimethylurea and N,N'diethylurea are in solid form.

3. The method according to claim 1, wherein said N,N'-dimethyurea and N,N'-diethylurea are nitrated together.

4. The method according to claim 2, wherein said N,N'-dimethyurea and N,N'-diethylurea are nitrated together.

5. The method according to claim 1, wherein the dinitrodimethylurea, dinitrodiethylurea and other reaction products are collected in dichloromethane by countercurrent extraction.

6. The method according to claim 2, wherein the dinitrodimethylurea, dinitrodiethylurea and other reaction products are collected in dichloromethane by countercurrent extraction.

7. The method according to claim 3, wherein the dinitrodimethylurea, dinitrodiethylurea and other reaction products are collected in dichloromethane by countercurrent extraction.

8. The method according to claim 4, wherein the dinitrodimethylurea, dinitrodiethylurea and other reaction products are collected in dichloromethane by countercurrent extraction.

9. The method according to claim 1, wherein said dinitrodimethylurea and dinitrodiethylurea are hydrolyzed together.

10. The method according to claim 2, wherein said dinitrodimethylurea and dinitrodiethylurea are hydrolyzed together.

11. The method according to claim 3, wherein said dinitrodimethylurea and dinitrodiethylurea are hydrolyzed together.

12. The method according to claim 4, wherein said dinitrodimethylurea and dinitrodiethylurea are hydrolyzed together.

13. The method according to claim 5, wherein said dinitrodimethylurea and dinitrodiethylurea are hydrolyzed together.

14. The method according to claim 6, wherein said dinitrodimethylurea and dinitrodiethylurea are hydrolyzed together.

15. The method according to claim 7, wherein said dinitrodimethylurea and dinitrodiethylurea are hydrolyzed together.

16. The method according to claim 8, wherein said dinitrodimethylurea and dinitrodiethylurea are hydrolyzed together.

17. The method according to claim 9, wherein dinitrodimethylurea and dinitrodiethylurea are hydrolyzed in common at about 100° C. in the desired molar ratio.

18. The method according to claim 10, wherein dinitrodimethylurea and dinitrodiethylurea are hydrolyzed in common at about 100° C. in the desired molar ratio.

19. The method according to claim 11, wherein dinitrodimethylurea and dinitrodiethylurea are hydrolyzed in common at about 100° C. in the desired molar ratio.

20. The method according to claim 12, wherein dinitrodimethylurea and dinitrodiethylurea are hydrolyzed in common at about 100° C. in the desired molar ratio.

21. The method according to claim 13, wherein dinitrodimethylurea and dinitrodiethylurea are hydrolyzed in common at about 100° C. in the desired molar ratio.

22. The method according to claim 14, wherein dinitrodimethylurea and dinitrodiethylurea are hydrolyzed in common at about 100° C. in the desired molar ratio.

23. The method according to claim 15, wherein dinitrodimethylurea and dinitrodiethylurea are hydrolyzed in common at about 100° C. in the desired molar ratio.

24. The method according to claim 16, wherein dinitrodimethylurea and dinitrodiethylurea are hydrolyzed in common at about 100° C. in the desired molar ratio.

25. A method for producing DNDA-5-7 comprising
    nitrating N,N'-dimethylurea and N,N'-diethylurea together to form dinitromethylurea and dinitroethylurea with highly concentrated nitric acid wherein said N,N'-dimethylurea and N,N'-diethylurea are in solid form and are in a molar ratio of about 2:1;
    hydrolyzing said dinitrodimethylurea and dinitrodiethylurea together; and
    condensing the methylnitramine and ethylnitramine to form DNDA.

26. The method of claim 1 wherein said process is continuous.

27. The method of claim 25 wherein said process is continuous.

28. A method of preparing a propellant charge powder comprising
    producing DNDA-5-7 by nitrating in common N,N'-dimethylurea and N,N'-diethylurea to form dinitromethylurea and dinitroethylurea with highly concentrated nitric acid wherein said N,N'-dimethylurea and N,N'-diethylurea are in solid form and are in a molar ratio of about 2:1;
    hydrolyzing said dinitrodimethylurea and dinitrodiethylurea together; and
    condensing the methylnitramine and ethylnitramine to form DNDA; and
    admixing the DNDA to form a propellant charge powder.

29. A method for preparing propellant charge powder comprising:
    producing DNDA by nitrating N,N'-dimethylurea and N,N'diethylurea with highly concentrated nitric acid,
    hydrolyzing the dinitrodimethylurea and dinitrodiethylurea to produce methylnitramine and ethylnitramine and other reaction products; and
    condensing the methylnitramine and ethylnitramine to form DNDA; and
    admixing the DNDA to form a propellant charge powder.

30. The method of claim 1 wherein said highly concentrated nitric acid is 100% nitric acid.

31. The method of claim 25, wherein said highly concentrated nitric acid is 100% nitric acid.

32. The method of claim 28, wherein said highly concentrated nitric acid is 100% nitric acid.

33. The method of claim 29, wherein said highly concentrated nitric acid is 100% nitric acid.

34. A method consisting of:
    nitrating both, N,N'-dimethylurea and N,N'diethylurea with highly concentrated nitric acid to produce dinitrodimethylurea
    hydrolyzing the dinitrodimethylurea and dinitrodiethylurea to produce methylnitramine and ethylnitramine and other reaction products; and
    condensing the methylnitramine and ethylnitramine to form DNDA.

* * * * *